(12) United States Patent
Arbault et al.

(10) Patent No.: US 8,515,523 B2
(45) Date of Patent: Aug. 20, 2013

(54) ELECTROCHEMICAL DEVICE AND METHOD FOR MEASURING THE REDOX STATE OF THE SKIN

(75) Inventors: Stéphane Arbault, Nogent sur Marne (FR); Cécile Pebay, Paris (FR); Christian Amatore, Paris (FR); Nadège Lachmann-Weber, Checy (FR); Catherine Heusele, Limours (FR); Isabelle Renimel, Trainou (FR)

(73) Assignees: L V M H Recherche, Saint Jean de Braye (FR); Ecole Normale Superieure, Paris (FR); Centre National de la Recherche Scientifique, Paris Cedex (FR)

( * ) Notice: Subject to any disclaimer, the term of this patent is extended or adjusted under 35 U.S.C. 154(b) by 1311 days.

(21) Appl. No.: 12/159,051

(22) PCT Filed: Dec. 22, 2006

(86) PCT No.: PCT/FR2006/002863
§ 371 (c)(1),
(2), (4) Date: Jun. 24, 2008

(87) PCT Pub. No.: WO2007/077360
PCT Pub. Date: Jul. 12, 2007

(65) Prior Publication Data
US 2008/0294026 A1    Nov. 27, 2008

(30) Foreign Application Priority Data

Dec. 26, 2005  (FR) .................................. 05 13339

(51) Int. Cl.
*A61B 5/05* (2006.01)
*A61B 5/04* (2006.01)
(52) U.S. Cl.
USPC ........................................................ 600/393

(58) Field of Classification Search
None
See application file for complete search history.

(56) References Cited

U.S. PATENT DOCUMENTS

| 4,932,410 | A | 6/1990 | Lacourciere et al. |
| 6,108,570 | A | 8/2000 | Kohen et al. |
| 2004/0018486 | A1 | 1/2004 | Dunn et al. |

FOREIGN PATENT DOCUMENTS

| FR | 2845264 | 4/2004 |
| GB | 1587879 | 4/1981 |
| JP | 2000/028764 A | 1/2000 |

OTHER PUBLICATIONS

FR 2845264 A1, computer translation, 2004.*
French Preliminary Search Report; European Patent Office; Jul. 25, 2006; EPO Form 1503.
International Search Report, European Patent Office, May 16, 2007; Form PCT/ISA/210.

* cited by examiner

*Primary Examiner* — Brian J Gangle
(74) *Attorney, Agent, or Firm* — Miller, Matthias & Hull LLP

(57) ABSTRACT

The present inventor relates to an electrochemical device for measuring the redox state of the skin, comprising at least one working electrode, such as a microelectrode, a counter electrode, and a reference electrode, said electrodes all being fixed into a single support intended to allow each of said electrodes to be simultaneously brought into contact with the surface of the skin to be tested, the electrodes being connected, on the one hand, to a means for imposing a defined voltage between the working electrode and the reference electrode, such as a potentiostat, and, or the other hand, to a device for measuring the intensity of the current generated at the working electrode by the detection of redox species. The invention also related to a method of measuring the redox state of the skin.

32 Claims, 7 Drawing Sheets

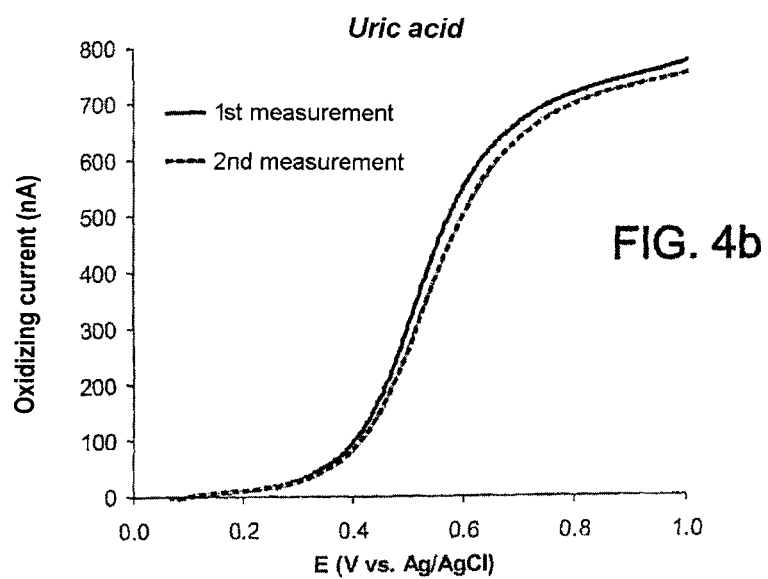
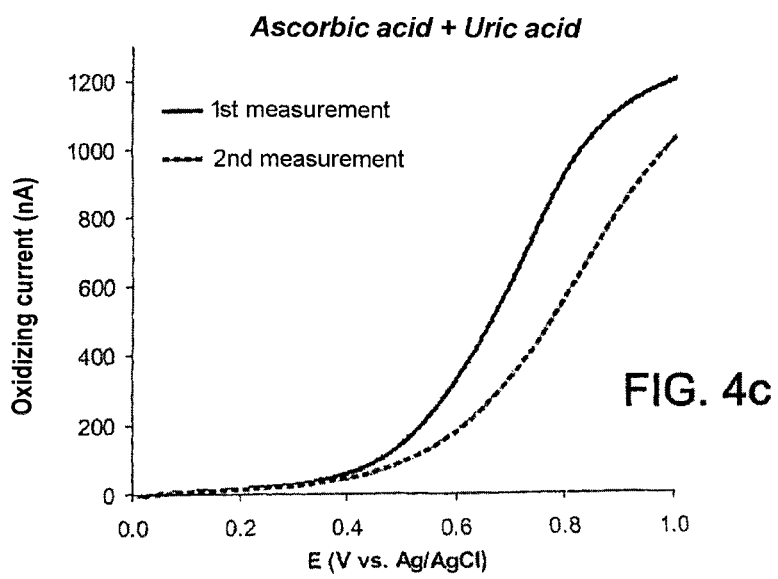

ELECTROCHEMICAL DEVICE AND METHOD FOR MEASURING THE REDOX STATE OF THE SKIN

CROSS-REFERENCE TO RELATED APPLICATION

This is a 35 USC §371 National Stage Application of International Patent Application No. PCT/FR2006/002863 filed on Dec. 22, 2006, which claims priority under the Paris Convention to French Patent Application No. FR 05 12740, filed on Dec. 26, 2005.

FIELD OF THE DISCLOSURE

The invention relates to an electrochemical device for and an electrochemical method of non-invasive real-time measurement of the redox state of the surface of the skin. It also pertains to the application of this method to the determination of the efficacy of a cosmetic product on the redox state of the skin, in other words on the effects of controlling oxidative stresses and skin aging.

BACKGROUND OF THE DISCLOSURE

Like the rest of the body, the skin ages. This cutaneous aging is manifested more particularly in the appearance of wrinkles, brown spots, etc, which are the visible consequences of disturbances to the cell metabolism and to the organization of the extracellular matrix.

The cause of this aging is both biological and environmental.

In its role as a barrier to external attack, the skin is subjected to major environmental stresses, and more particularly to oxidative stress.

In order to control this oxidative stress, natural systems of regulation and protection exist that are either enzymatic in nature (superoxide dismutases, catalase, peroxidases) or else nonenzymatic in nature, such as low molecular weight antioxidants, which are, for example, vitamin E, vitamin C, and glutathione.

These antioxidant species may be found in the surface layers of the skin.

At the surface of the skin, its antioxidant species, i.e., reductive species, react with the oxidative species that attack the skin. The quantity and the nature of these oxidative and reductive species present on the surface of the skin determine the redox state of the skin.

It is therefore advantageous to be able to analyze these species qualitatively and to quantify them in order to gain knowledge of the mechanisms of control of oxidative stress and to have an evaluation of the state of skin aging.

The measurement of reductive species at the surface of the skin has already been studied by electrochemical methods:
  either by indirect measurement: an extraction solution is contacted with the skin for a predetermined time and then the oxidoreductive species are assayed by cyclic voltammetry (Kohen et al. (1999) Methods in Enzymology, 300, 428-437),
  or with a set of a number of electrodes which are contacted with the skin (U.S. Pat. No. 6,108,570 by Kohen et al.; or FR 2 845 264, which describes a "device and method for direct measurement of pH and of oxidation state" by means of a working electrode and an auxiliary electrode, which may be grouped together either in the same capillary or in two concentric capillaries, a reference electrode being used, furthermore, independently and separately).

These prior art devices either do not allow direct measurements or else are not simple to employ, given that they require the application of different electrodes to the skin. Furthermore, they are applied to very small skin surface areas.

There is therefore a real need for a device which is simple to use and allows effective control over the operating conditions and hence good reproducibility, and which allows homogeneous measurement over a representative portion of the skin. This device shall, moreover, allow continuous and noninvasive measurement of the redox state of the skin.

SUMMARY OF THE DISCLOSURE

The present inventors, following long and in-depth research, have found that these various requirements can be met by means of an electrochemical device comprising:
  at least one working electrode,
  a counterelectrode,
  a reference electrode,
said electrodes all being fastened in a single support intended to allow each of said electrodes to be contacted simultaneously with the surface of the skin to be tested, the electrodes being connected on the one hand to a means allowing a defined voltage to be applied between the working electrode and the reference electrode, such as a potentiostat, and on the other hand to a device for measuring the intensity of the current generated at the working electrode by the detection of redox species.

The device of the invention is thus very simple to use, given that it allows the three electrodes to be contacted simultaneously with the surface of the skin.

In the present invention the terms "electrochemical device" and "sensor" will be used synonymously.

By "skin contact" or "contact with the skin" is meant, in the present invention, direct or indirect contact between the electrodes and the surface of the skin. The electrodes are in direct contact with the skin when at least part of their active surface area touches the surface of the skin. The electrodes are in indirect contact with the skin when at least part of their active surface area is in contact with a fluid which is itself deposited on the surface of the skin.

"Low molecular weight antioxidants" are reducing agents such as glutathione, ascorbic acid, tocopherols, carnosine, uric acid, vitamin E, phenols and other molecules small in size.

BRIEF DESCRIPTION OF THE DRAWINGS

The description which follows of various embodiments of the device of the invention should be read in relation to the attached drawings, wherein:

FIG. 4b is a graph depicting oxidizing current vs. potential difference, obtained in vitro, and with respect to uric acid;

FIG. 4c is a graph depicting oxidizing current vs. potential difference, obtained in vitro, and with respect to ascorbic and uric acid;

DETAILED DESCRIPTION

The subject matter of the invention is an electro-chemical sensor combining 3 electrodes: a working electrode, a reference electrode and a counter-electrode. This sensor, with a total surface area of several $mm^2$ to several $cm^2$, is contacted with the skin and allows the redox state of the surface of the skin, and also the effect of the treatment by a pharmaceutical or cosmetic product on this redox state, to be measured non-invasively and in real time.

Figure 1:
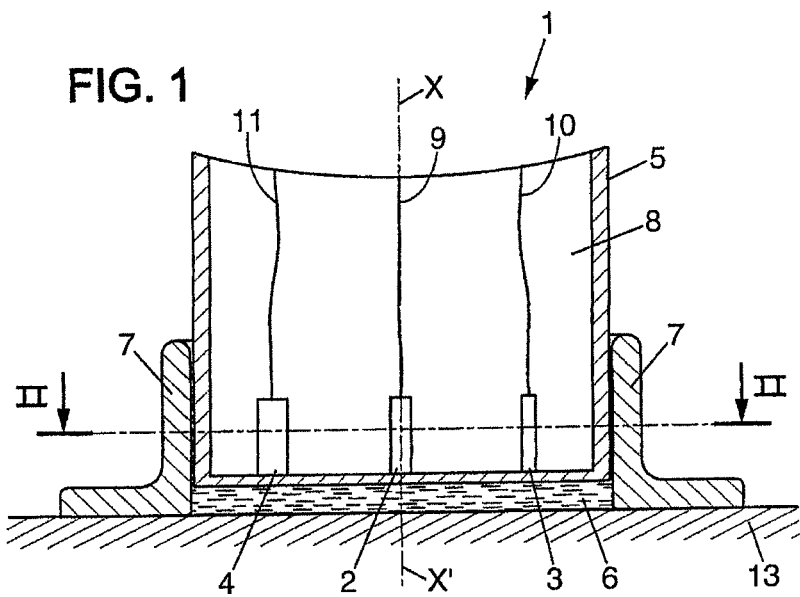
FIG. 1 represents in cross section along the axis I-I in FIG. 2 a device according to a first embodiment of the invention.
Figure 2:
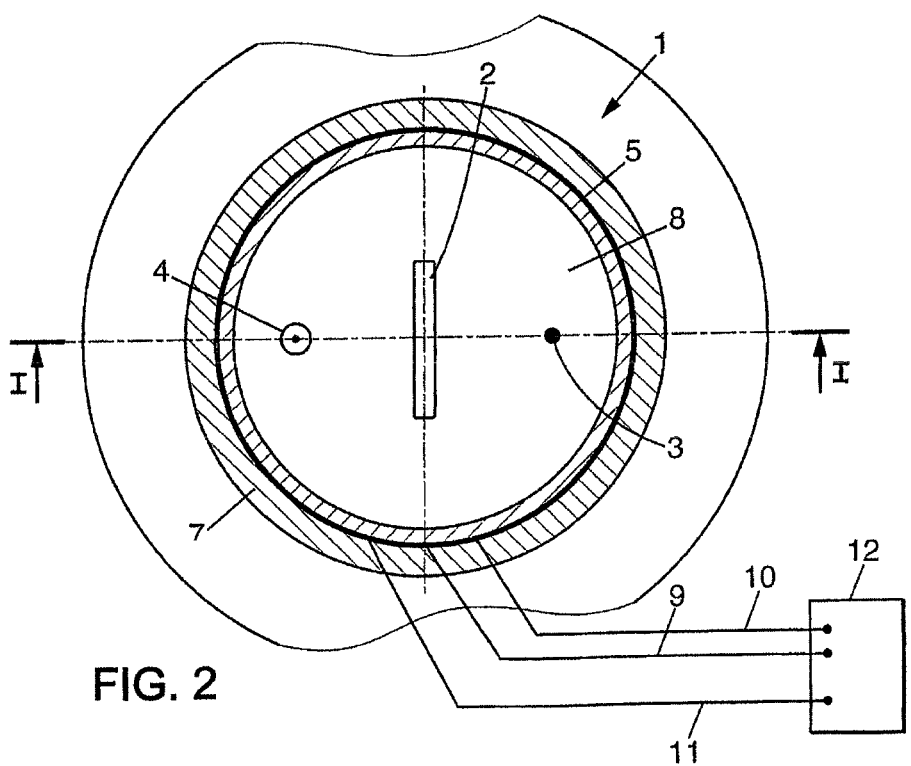
FIG. 2 represents in cross section along the axis II-II of FIG. 1 a device according to a first embodiment with cup removed.

FIGS. 1 and 2 show an embodiment of the part of the device 1 of the invention which comes into contact directly with the skin, or indirectly, in other words via an electrically conductive contact liquid which is present in a cup that is placed on the skin (shown only in FIG. 1).

The device 1 comprises a planar platinum electrode 2, a platinum wire which constitutes the counterelectrode 3, and an Ag/AgCl reference electrode 4.

These three electrodes 2, 3 and 4 are disposed in a cylindrical body 5 whose end is in contact with the skin or with the liquid 6 filling the cup 7. According to one preferred embodiment, shown in FIGS. 1 and 2, the internal diameter of the cup 7 is adapted to the external diameter of the cylindrical body 5, so that the cup 7 is in contact with the cylindrical body 5.

The three electrodes are held fastened to the inside of the cylindrical body 5 by a resin 8, an epoxy resin for example.

The three electrodes are disposed such that the active surface of each of them is flush within a single plane, preferably perpendicular to the longitudinal axis (X X').

Each of the electrodes 2, 3, and 4 is connected by a conductive wire 9, 10, and 11, respectively, to a potentiostat 12 (shown only in FIG. 2). The cup 7 is placed on the surface 13 of the skin to be tested.

According to one particular embodiment the surface area of the support is from 100 $mm^2$ to 10 $cm^2$, preferably from 150 $mm^2$ to 5 $cm^2$, and more preferably from 200 $mm^2$ to 2 $cm^2$.

By "support surface" is meant the surface that the support occupies when the sensor is positioned in operations such that the electrodes are in contact with the surface of the skin or the contact liquid. This support surface corresponds to the area of skin to be tested.

The working electrode is a microelectrode, in other words an electrode whose active part has a size at least in the range of approximately 1 μm to approximately 50 μm.

The shape of the working electrode depends on the technology employed for its manufacture. Thus the working electrode may, for example, be ring-, strip-, disk- or ellipse-shaped or conical.

The active surface of the working electrode, in other words the active part of the working electrode, may or may not be planar. This surface is adapted as a function of the resolution desired for the measure-ments. The greater the surface area, the less the quality of the resolution in signal-to-noise ratio, but the greater the extent to which the result will be representative of the average redox state of the skin.

According to one advantageous embodiment it is possible to dispose a plurality of working electrodes in the support. In that case these working electrodes will be distributed regularly within the support, in other words, in application on the surface of the skin, so as to optimize the resolution.

The active surface area of the working electrode or the sum of the surface areas of the working electrodes is between 100 and 10 000 $μm^2$, preferably between 200 to 3000 $μm^2$.

The ratio between the active surface area of the working electrode or the sum of the active surface areas of the working electrodes and the surface area of skin tested may be of the order of $10^{-3}$ to $10^{-5}$, preferably of $10^{-4}$ to $10^{-5}$.

The active surface of the working electrode is made of carbon or of metal, the constituent metal being selected from the group consisting of gold, platinum, iridium, tungsten, and palladium, preferably platinum, or an alloy of these metals, or an alloy of these metals with an oxide of these metals, or with a metal oxide, preferably a transition metal oxide such as tin oxide. Examples of alloys which can be used are platinum/iridium, iridium/tin oxide, and platinum/tungsten alloys. Preferably, when the device comprises two or more working electrodes, said electrodes are all made of the same material.

It will be appreciated that only the nature of the active surface of the electrode is important. Accordingly the electrode may have a non-metal core, made of carbon, for example, which is covered with a metal.

In order to optimize the results, to limit the passivation of the surface of the working electrode, and to increase its sensitivity, it is preferably modified by a deposit of platinum black, in which case the electrode is said to be platinized. This deposit is produced by electrolysis, on the surface of the working electrode, of a solution of platinum salts, to form one or more layers of solid polycrystalline metal, of high active surface area and high electrocatalytic activity. In the same way, the active surface of the working electrode may be covered with a deposit of gold or of chromium.

The reference electrode is an Ag/AgCl electrode, a calomel electrode or a reference pseudoelectrode such as a platinum wire.

The counterelectrode is a platinum metal wire, or is made of stainless metal alloys such as of stainless steel, or of non-oxidizing conductive ceramic. It is preferably made of platinum or of stainless steel.

The electrodes are fastened in a single support by any means which, of course, ensures electrical insulation between said electrodes. One entirely advantageous fastening means is an electrochemically and chemically inert insulating resin, such as an epoxy resin.

According to one advantageous embodiment it is possible to place the electrodes in indirect contact with the skin in such a way as to prevent any measurement error due to excess pressure on the skin, for example, or to heterogeneous or inadequate contact between the skin and the sensor. For this purpose, the device in accordance with the invention may comprise a means allowing a predetermined quantity to be contained of liquid which makes contact on the one hand with the skin in the use position and on the other hand with the support.

In one preferred embodiment the sensor is inserted into an open-based cup which is intended to be adhered to the skin. A small volume of contact liquid is placed in the cup adhered to the skin in order to ensure contact between the skin and the electrodes.

Figure 3:
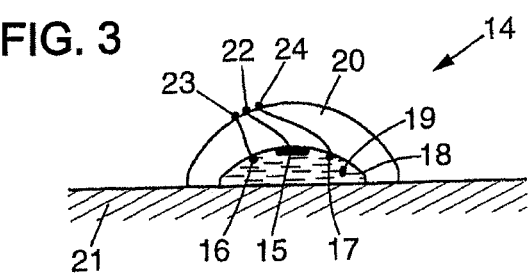
FIG. 3 represents in cross section a device according to a second embodiment of the invention.

According to a second embodiment, as illustrated in FIG. 3, said means allowing a skin contact liquid to be contained is an integral part of the support.

The advantages associated with the use of a liquid reservoir are multiple: absence of pressure of the electrode on the skin during measurement, analyses under standardized physico-chemical operating conditions, and control of the surface area of skin that is measured. The reproducibility of the measurements is enhanced. Kinetics may be conducted over several tens of minutes and may thus enhance the sensitivity of the technique.

The contact liquid is an electrical conductor, especially an ionic conductor, which has a very varied viscosity from 0.8 mPas to 10 Pas. This liquid may be, for example, an aqueous, alcoholic, aqueous-alcoholic or oily medium, or an emulsion of, for example, water, ethanol, a water/ethanol solution, liquid petrolatum, silicone oil or vegetable oil, said medium having been made conductive, if necessary, by salification using, for example, NaCl.

The viscosity of the liquid may be modified by addition of at least one gelling agent which does not influence the conductivity of the liquid but acts as a viscosity modifier. A gelling agent of this kind may be selected from the group comprising gelling agents which are compatible with skin use, such as, more particularly, carbopol, natural gum, alginates, cellulose derivatives, and hyaluronic acid.

The liquid may be buffered and preferably has a pH of 4 to 8, preferably of 5 to 7.5.

Depending on the chemical nature of the liquid that is used, the sensor will allow measurement of the release kinetics of several types of oxidoreductive species present on the surface of the skin. For example, a liquid based on ethanol is entirely appropriate for assaying vitamin E.

The amount of liquid depends, of course, on the size of the support.

The amount of contact liquid may be very low. Hence amounts of the order of $10^{-5}$ to $10^{-3}$ L/cm$^2$ of skin surface area to be tested, in other words the skin surface area delimited by the support, may prove sufficient. Preferably, and practically, this volume may be of the order of $10^{-4}$ to $5 \times 10^{-4}$ L/cm$^2$.

FIG. 3 shows a device 14 according to a second embodiment of the invention. This device 14 comprises a planar platinum working electrode 15, a platinum counterelectrode 16, and an Ag/AgCl reference electrode 17.

These three electrodes 15, 16, and 17 are arranged on the internal surface 18, which forms a cavity and is filled with contact liquid 19, of the casing 20.

The casing 20 is rounded or rectangular in shape and comprises a cavity. In the use position, the casing is placed on the skin such as to form a closed space between said casing and the skin 21. This space (or cavity) is filled with liquid 19 for the purpose of realizing the measurements.

Each of the three electrodes 15, 16, and 17 is connected to the outer surface of the support at a connection point 22, 23, and 24 respectively. These connection points allow information to be transmitted to a detection apparatus, which is not shown.

The invention likewise relates to a method of measuring the redox state of the skin.

By "redox state" of the skin, is meant the quantitative and/or qualitative determination of reductive species which are present on the surface of the skin.

This determination may be made either in vivo or in vitro, using artificial skin, i.e., skin or epidermis which has been reconstituted by cell culture, or else a sample of epidermis or of skin on a living being.

The reductive species measured are, for example, the low molecular weight antioxidants described earlier.

The measurement method consists in the following steps:
disposing the device on the skin, preferably immobilizing it,
applying a voltage between the working electrode and the reference electrode,
measuring the intensity of the current at the working electrode that is due to the redox species.

It is possible to apply either a constant or a variable voltage. The voltage applied may be between −1 and 2 V, preferably between 0 and 1.5 V, and more preferably between 0 and 1.0 V. The variation in the voltage over time is a function of the desired application; for example, it may be varied either linearly over time or else discontinuously between two values or a plurality of successive values.

In one advantageous method the technique of cyclic sweep voltammetry is used, which consists in varying the voltage linearly over time, within a given range, between the minimum value and the maximum value and then from the maximum value to the minimum value.

According to one advantageous embodiment the method further comprises a step intended to fix in place a means allowing a contact liquid to be contained between the skin and the electrodes.

The method of the invention may make it possible to carry out one measurement at a given moment or may make it possible to carry out several measurements over time so as to have cumulative values or in order to better quantify a change over a given period, which values may be more readily interpreted.

Accordingly, different measurements may be made at different times t, it being possible for t to range from a number of seconds to several months.

The method of the invention may further comprise an additional step of comparing intensity curves obtained with reference curves or control curves.

In another aspect the invention relates to a method of determining the efficacy of a cosmetic product for topical application to the skin that is intended to control the effects of oxidative stress. This method consists in measuring the redox state of the skin at a time to by means of the method according to the invention, in applying a cosmetic product one or more times to a defined area of the skin, this application being preferably regular, and then in measuring the redox state of the skin at a given time T subsequent to the last application of the cosmetic product, by means of the method of the invention, and in comparing the results obtained at the time t0 and at the time T.

The invention likewise relates to a method of determining the efficacy of a product intended for controlling the effects of oxidative stress that consists in measuring the redox state of the skin at a time t0 by means of the method according to the invention, in applying said product topically to the skin or in administering it, one or more times, then in measuring the redox state of the skin at a given time T subsequent to the last application of said product, by means of the method of the invention, and in comparing the results obtained at the time t0 and at the time T.

The products which may be tested in this way are dermatological, pharmaceutical or cosmetic products which are intended more particularly for topical application or for oral administration.

The time T is of course dependent on the nature of the products used. For example, if the product in question is an immediate-effect product, the time T may be from a few minutes to a few hours. If, on the other hand, the product in question is a long-term-effect product, this time T may be from a few days to a few months.

When the products in question are topical products, the efficacy may be measured by applying the product, regularly for example, to an area of skin of the volunteer and, at the time t0 and then at the time T, a measurement may be carried out on this area of skin and on an equivalent area of skin which has not received the regular application. In this way the results obtained on these two areas will be readily comparable. It is possible, for example, to choose to apply the product to the front face of the left forearm and to carry out the measurements on each of the forearms. In order to obtain results which are statistically reliable, a sufficient number of volunteers are used, and the applications are made to the left forearm of half of the volunteers and to the right forearm of the other half of the volunteers.

According to another embodiment the invention relates to a method of determining the redox state of the skin subsequent to a stress, which consists in measuring the redox state of the skin at a time to by means of the method according to the invention, in applying this stress one or more times, and then in measuring the redox state of the skin at a given time T, subsequent to the final application of said stress, by means of the method of the invention, and in comparing the results obtained at the time t0 and at the time T.

Examples of stresses which can be applied and whose effect can be measured directly include radiation such as UV, more particularly UVA, and IR, chemical stresses due, for example, to hydrogen peroxide or to benzoyl peroxide, thermal stresses due, for example, to extreme temperatures, and mechanical stresses due, for example, to friction.

The invention may also make it possible to determine the capacity of the skin to recover its protective abilities after a stress, by a method which consists:
in a first step, in measuring the redox state of the skin at a time to by means of the method according to the invention,
in a second step, in applying said stress one or more times in the presence or absence of treatment,
in a third step, in determining, by means of measurements with the aid of the method according to the invention, the time t1 corresponding to the appearance of the maximum effect of said stress on the redox state of the skin,
in a fourth step, in measuring, with the aid of the method according to the invention, the redox state of the skin at a number of times ti, i being greater than 1,
and finally, in a fifth step, in determining the kinetics of return of the redox state of the skin to its basal redox state, from the result obtained at the time t0, which corresponds to the basal redox state of the skin, and the results obtained at the times t1 and ti.

The value i will of course vary as a function of the nature of the stress and of its intensity, and of the nature of the treatment used. The intervals between the different values ti may be identical or different. This is because it may prove advantageous to measure the change over time of the effect of the application of the stress, following the above-defined measurement at the time t1, at times t2, t3, and t4 which are close to the time t1 and are separated by very short intervals (from a few minutes to a few tens of minutes), for example, and then to space out the following measurements, for example, with t5 and t6 able to be very much greater (of the order of 1 hour to a few hours or even 1 day to several days).

The device according to the invention may also be employed in a method of determining the redox state of a sample which is representative of a population.

In this case, a sample which is representative of a certain population, for example of persons with a very dark skin color, such as persons whose skin is of phototype VI, aged from 45 to 60 years, or of persons of lighter skin, of phototype III for example, aged from 20 to 25 years, is selected and the redox state of the skin of each of the volunteers from each population is measured in order to collect statistical data.

The invention may also make it possible, in epidemiological study, to determine the effect of a stress suffered accidently or associated with a particular lifestyle (UV, nuclear radiation, pollution, etc) or with a pathology, etc.

The invention will be described in greater detail in the examples which follow, which are given solely by way of illustration of the invention, and which are not limitative.

EXAMPLES

In the examples a sensor according to the invention is used which is as described in FIG. 1 or 2.

The dimensions are as follows:
length of the cross section of the support =10 cm,
working electrode, in the form of a planar strip 100 μm long and 5 μm wide,
counterelectrode: planar platinum disk electrode 500 μm in diameter,
reference electrode: planar disk electrode of Ag/AgCl type, 500 μm in diameter,
cup 1.5 cm in diameter, having an opening 1 cm in diameter.

The cup, of Radiometer Analytical brand, includes a collar for nonpermanent adhesive fastening to the skin.

The potentiostat is an instrument sold by Ensmann Instruments (Bloomington, Ind., USA under the reference EI400). The intensity is recorded using a Powerlab 4SP digital/analog interface and the software Chart 5.0 for PC which is sold by AD Instruments (Colorado Springs, Colo., USA).

Examples 1 to 3 are carried out in vitro and examples 4 and 5 in vivo.

Example 1

By means of the device according to the invention, employing a platinum strip electrode as working electrode, the following analyses were carried out by linear sweep voltammetry of the potential (10 mv·s$^{-1}$):
Test 1: of ascorbic acid at 2 mM in PBS,
Test 2: of uric acid at 2 mM in PBS,
Test 3: of a 50/50 mixture of uric acid at 2 mM and ascorbic acid at 2 mM in PBS.

Test 1 was carried out 3 times in succession without rinsing or cleaning of the electrode.

Tests 2 and 3 were each carried out 2 times in succession without rinsing or cleaning of the electrode.

Figure 4A:
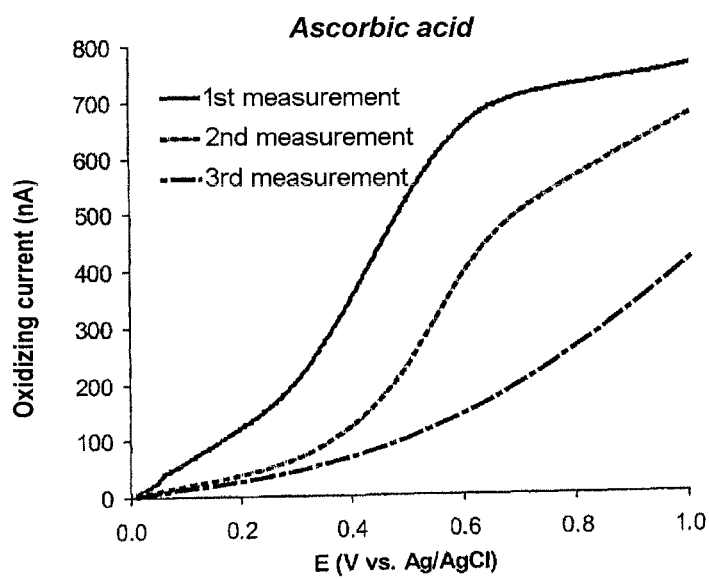
FIG. 4a is a graph depicting oxidizing current vs. potential difference, obtained in vitro, and with respect to ascorbic acid.

The results obtained are shown, respectively, in FIGS. 4*a*, 4*b*, and 4*c*.

From these figures it is apparent that the oxidation product of ascorbic acid passivates the surface of the platinum electrode.

A mixture of ascorbic acid and uric acid would therefore be difficult to measure reliably with a platinum working electrode.

Example 2

Tests 1 and 2 of example 1 are repeated but using as the working electrode a platinized platinum strip electrode.

Figure 5A:
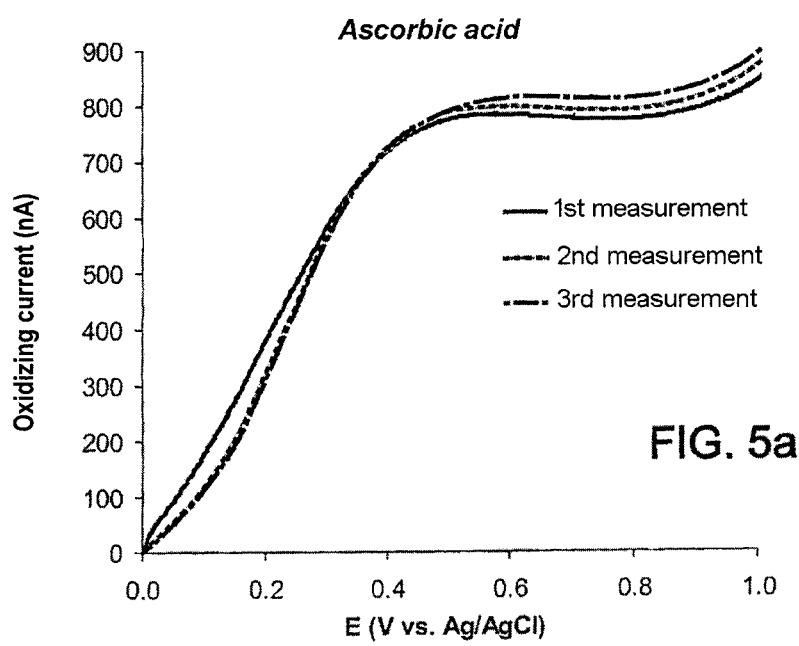
FIG. 5a is a graph similar to FIG. 4a but using a platinized platinum strip as the working electrode.
Figure 5B:
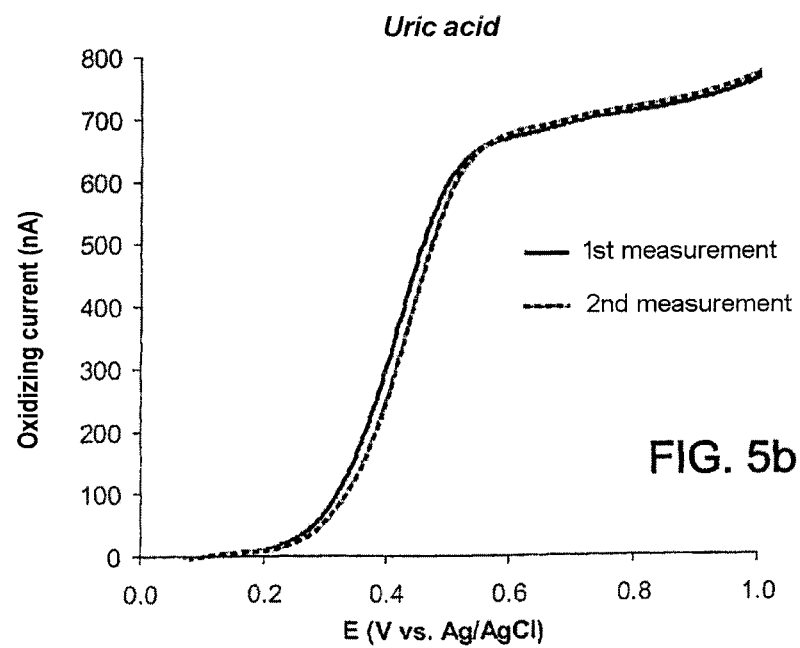
FIG. 5b is a graph similar to FIG. 4b but using a platinized platinum strip as the working electrode.

The results obtained are shown in FIGS. 5a and 5b.

In these figures it is apparent that the platinized platinum electrode allows the passivation by the oxidation product of ascorbic acid to be avoided and offers stable and reproducible detection of ascorbic acid and of uric acid.

Example 3

An analysis by linear sweep voltammetry of the potential ($10 \, mv \cdot s^{-1}$) in PBS is carried out using a device in accordance with the invention with a platinized platinum strip working electrode, which bears a cup (according to FIG. 1) (test 3-1) and using a prior-art device in which the counterelectrode and the working electrode are placed in a cup and the reference electrode is placed in PBS outside the cup (test 3-2).

The cups of tests 3-1 and 3-2 are each filled with 200 µl of PBS.

Figure 6A:
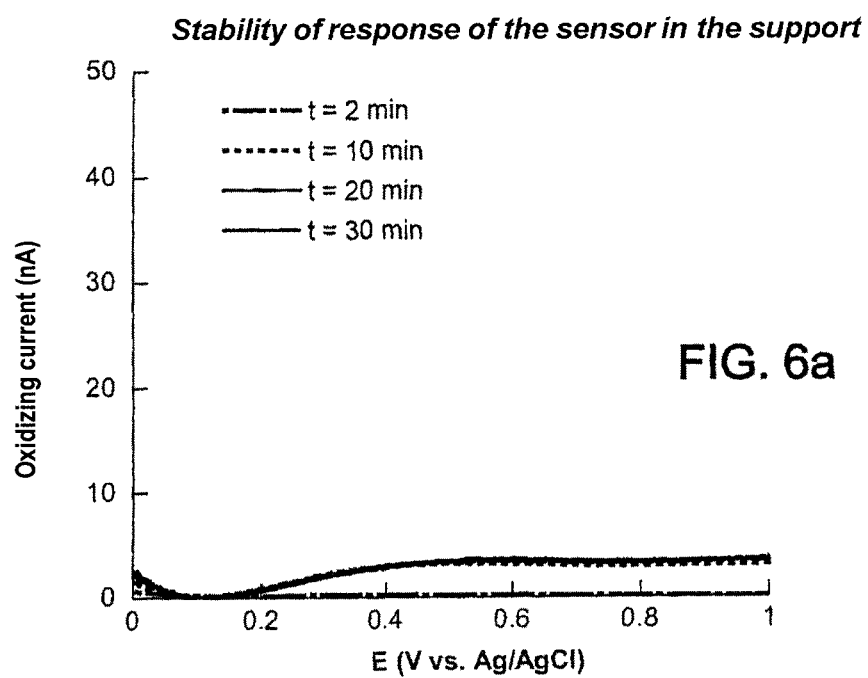
FIG. 6a is a graph plotting oxidizing current vs. potential difference, obtained in vitro, and depicting stability of response of the sensor in the support.
Figure 6B:
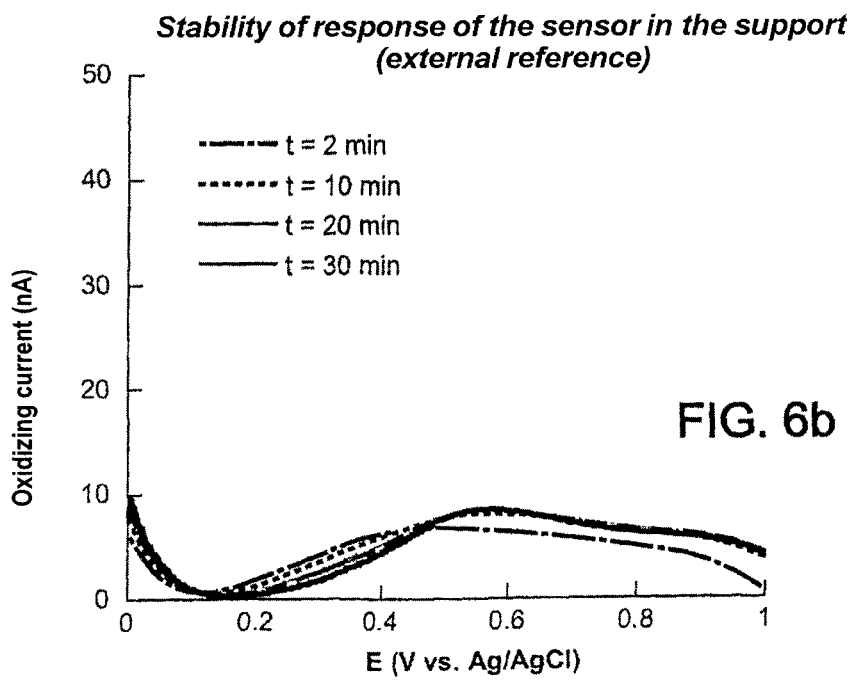
FIG. 6b is a graph similar to FIG. 6a but with an external reference.

Four analyses by voltammetry are carried out for each test, at 2 min, 10 min, 20 min, and 30 min. The results are shown respectively in FIGS. 6a and 6b.

In these figures it is apparent that the stabilization is optimized with the device of the invention.

Example 4

The device employed comprises as its working electrode a platinized platinum strip electrode. It is placed in a cup which is adhered to the forearm of the volunteer. This cup is filled with 200 µl of physiological saline (test 4-1) and with 200 µl of PBS (test 4-2).

Figure 7A:
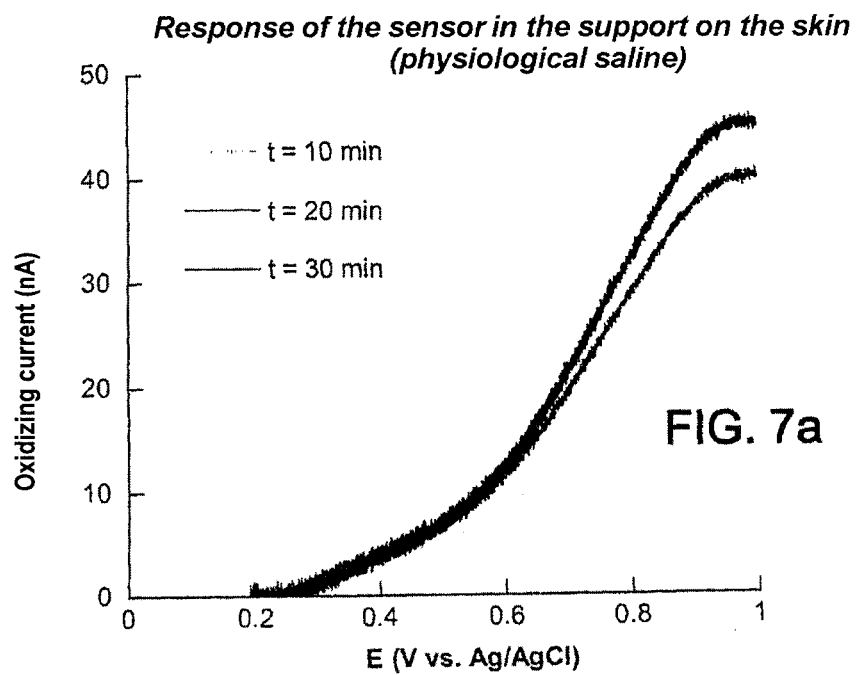
FIG. 7a is a graph plotting oxidizing current vs. potential difference, obtained for measurements made on the forearm of a volunteer and relative to physiological saline.
Figure 7B:
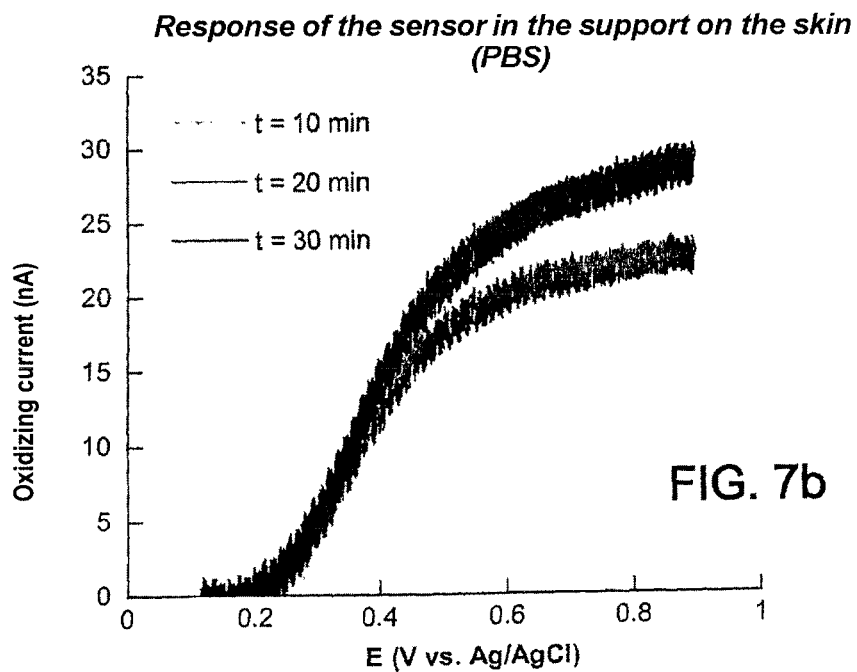
FIG. 7b is a graph plotting oxidizing current vs. potential difference, obtained for measurements made on the forearm of a volunteer and relative to PBS.

The measurements are carried out at the times t=10 min, 20 min, and 30 min. The curves of intensity as a function of the voltage applied are shown respectively in FIGS. 7a and 7b.

Example 5

Determination of the Efficacy of a Cosmetic Protective Care Cream

The purpose of the following test is to demonstrate the efficacy of a protective care cream, providing protection more particularly from oxidative stress. The care cream tested is a conventional oil-in-water emulsion containing an Orobranche rapum extract (0.5% by weight) and a *Combretum micranthum* leaf extract (0.1% by weight). The *Orobranche* extract possesses a well-known antioxidant activity (EP 0576420). The *Combretum* or *kinbeliba* extract also has antioxidant properties.

This cream is applied on D0 4 times every 2 hours to the left forearm of a volunteer, on a surface area of 25 cm$^2$, at a rate of 2 mg of cream per cm$^2$. Measurements are made 24 hours after the first application, i.e., 18 hours after the last application. The right forearm of said volunteer is not treated, and will serve as a control.

In this example, the device according to the invention with a platinized platinum strip working electrode is used, which is placed in a cup which is adhered to the forearm of the volunteer. This cup is filled with 200 µl of PBS.

Figure 8A:
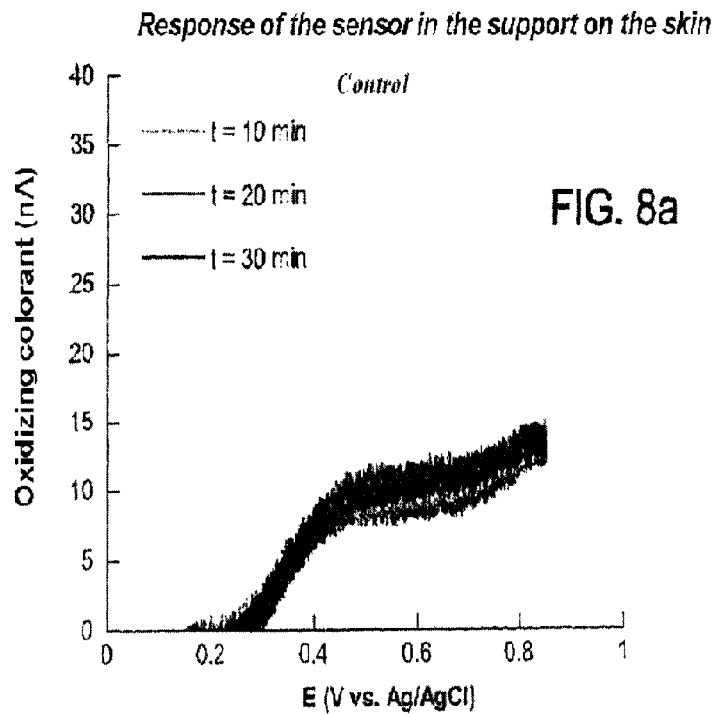
FIG. 8a is a graph plotting oxidizing current vs. potential difference, conducted on an untreated forearm.
Figure 8B:
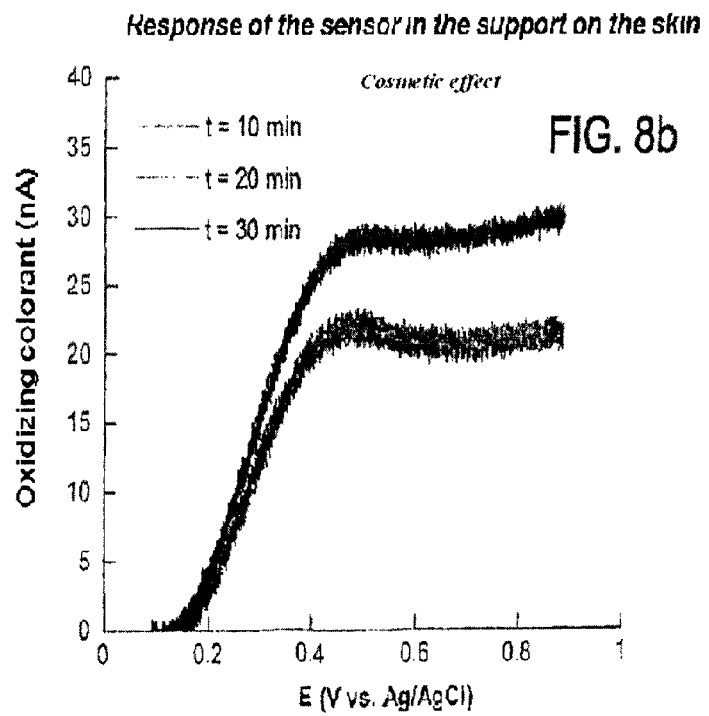
FIG. 8b is a graph plotting oxidizing current vs. potential difference, conducted on the control forearm.

Measurements were made on the part of the left forearm which had been treated and on the right forearm at the times 10 min, 20 min, and 30 min. The results are shown in FIG. 8, wherein FIG. 8a is obtained with the measurements conducted on the right (untreated) forearm and FIG. 8b with the results obtained by the measurements conducted on the left (control) forearm.

The invention claimed is:

1. An electrochemical device for measuring the redox state of the skin, comprising:
    at least one working electrode,
    a counterelectrode,
    a reference electrode,
    said electrodes all being fastened in a single support intended to allow each of said electrodes to be contacted simultaneously with the surface of the skin to be tested,
    the electrodes being connected on the one hand to a means allowing a defined voltage to be applied between the working electrode and the reference electrode, and on the other hand to a device for measuring the intensity of the current generated at the working electrode by the detection of redox species.

2. The device of claim 1, wherein the working electrode is a microelectrode.

3. The device of claim 1, wherein the active surface area of the working electrode or the sum of the surface areas of the working electrodes is between 100 and 10,000 µm$^2$.

4. The device of claim 1, wherein the ratio between the active surface area of the working electrode or the sum of the active surface areas of the working electrodes and the surface area of skin tested has an order of magnitude between $10^{-3}$ and $10^{-5}$.

5. The device of claim 1, wherein the working electrode is ring-, strip-, disk- or ellipse-shaped or is conical.

6. The device of claim 1, wherein the active surface of the working electrode is made of carbon or of metal, the constituent metal being selected from the group consisting of gold, platinum, iridium, tungsten, and palladium, an alloy of at least two of these metals, an alloy of at least two of these metals with an oxide of one of these metals and an alloy of at least one of these metals with a metal oxide.

7. The device of claim 1, wherein the active surface of the working electrode is made of platinized platinum.

8. The device of claim 1, wherein the reference electrode is selected from the group consisting in an Ag/AgCl electrode, a calomel electrode and a platinum-wire reference pseudo-electrode.

9. The device of claim 1, wherein the counterelectrode is a metal wire of platinum or stainless steel, or is of nonoxidizing conductive ceramic.

10. The device of claim 1, wherein the electrodes are fastened in the support by means of an electrochemically and chemically inert insulating resin.

11. The device of claim 1, further comprising a means allowing a predetermined quantity to be contained of ionic conductive liquid which, in the position of use, makes contact with the skin and contact with the support.

12. The device of claim 11, wherein the support and said means for allowing a skin contact liquid to be contained are made from a single piece of material.

13. The device of claim 11, wherein the skin contact liquid is an aqueous, alcoholic, aqueous-alcoholic or oily medium, or an emulsion said medium having been made conductive, if necessary, by salification.

14. The device of claim 11, wherein the contact liquid is buffered and has a pH of 4 to 8.

15. The device of claim 11, wherein the volume of contact liquid relative to the surface area of skin to be tested has an order of magnitude between $10^{-5}$ and $10^{-3}$ L/cm$^2$.

16. The device of claim 3, wherein the active surface area of the working electrode or the sum of the surface areas of the working electrodes is between from 200 to 3000 µm$^2$.

17. The device of claim 4, wherein the ratio between the active surface area of the working electrode or the sum of the active surface areas of the working electrodes and the surface area of skin tested has an order of magnitude between $10^{-3}$ and $10^{-5}$.

18. The device of claim 14, wherein the contact liquid is buffered and has a pH of 5 to 7.5.

19. The device of claim 15, wherein the volume of contact liquid relative to the surface area of skin to be tested has an order of magnitude between $10^{-4}$ and $5\times10^{-4}$ L/cm$^2$.

20. The device of claim 1, wherein the means allowing a defined voltage to be applied between the working electrode and the reference electrode is a potentiostat.

21. The device of claim 6, wherein the active surface of the working electrode is made of platinum.

22. The device of claim 6, wherein tha active surface of the working electrode is made of an alloy of at least on the metals selected from the group consisting of gold, platinum, iridium, tungsten, and palladium with a transition metal oxide.

23. The device of claim 13, wherein the skin contact liquid is an emulsion of water, ethanol, a water/ethanol solution, liquid petrolatum, silicone oil or vegetable oil.

24. The device of claim 13, wherein the medium has been made conductive, if necessary, by salification using NaCl.

25. A method of measuring the redox state of the surface of the skin, consisting in the following steps: disposing the device of claim 1 on the skin, applying a voltage between the working electrode and the reference electrode, measuring the intensity of the current at the working electrode that is due to the redox species.

26. The method of claim 25, wherein the voltage applied is between −1 and 2 V.

27. The method of claim 25, wherein different measurements are made at different times t, it being possible for t to range from a number of seconds to several months.

28. The method of claim 25, wherein the voltage is varied linearly over time, within a given range, between the minimum value and the maximum value and then from the maximum value to the minimum value.

29. The method of claim 25, wherein it further comprises an additional step of comparing the intensity curves obtained with reference curves or control curves.

30. The method of claim 26, wherein the voltage applied is between 0 and 1.5 V.

31. The method of claim 30, wherein the voltage applied is between 0 and 1.0 V.

32. A method for determining the redox state of a sample which is representative of a population, wherein the redox state of the skin is determined for each individual making up said sample using the device of claim 1.

\* \* \* \* \*